US011813189B2

(12) United States Patent
Hussey et al.

(10) Patent No.: US 11,813,189 B2
(45) Date of Patent: Nov. 14, 2023

(54) OSTOMY COLLECTION STATUS DETECTOR

(71) Applicant: Hussey Medical LLC, Waterville, ME (US)

(72) Inventors: Robert K. Hussey, Waterville, ME (US); David R. Hussey, Waterville, ME (US); Daniel K. Hussey, Windham, ME (US)

(73) Assignee: Hussey Medical, LLC, Waterville, ME (US)

( * ) Notice: Subject to any disclaimer, the term of this patent is extended or adjusted under 35 U.S.C. 154(b) by 127 days.

(21) Appl. No.: 17/110,686

(22) Filed: Dec. 3, 2020

(65) Prior Publication Data

US 2021/0169677 A1 Jun. 10, 2021

Related U.S. Application Data

(60) Provisional application No. 62/943,426, filed on Dec. 4, 2019.

(51) Int. Cl.
G01F 22/00 (2006.01)
A61F 5/44 (2006.01)
A61F 5/445 (2006.01)

(52) U.S. Cl.
CPC ............ *A61F 5/4404* (2013.01); *A61F 5/445* (2013.01); *G01F 22/00* (2013.01)

(58) Field of Classification Search
CPC .......... G01F 22/00; G01F 22/02; G01F 17/00; A61B 5/208; A61B 5/207; A61F 5/44;

(Continued)

(56) References Cited

U.S. PATENT DOCUMENTS 7,066,919 B1 *  6/2006  Sauerland ............... A61F 5/445
                                                            604/327
2013/0324952 A1 * 12/2013  Krystek .................. A61F 5/445
                                                            604/318

(Continued)

FOREIGN PATENT DOCUMENTS

CN       203719725 U   *  7/2014
GB         2510599 A      8/2014

(Continued)

OTHER PUBLICATIONS

Gmeinder, Gwen. How to Select a Custom Magnet Sensor. Jan. 8, 2016 [online], [retrieved on Nov. 30, 2022], Retrieved from the Internet <URL: https://www.allaboutcircuits.com/industry-articles/how-to-select-a-custom-magnet-sensor/> (Year: 2016).*

*Primary Examiner* — Erich G Herbermann
*Assistant Examiner* — Linnae E. Raymond
(74) *Attorney, Agent, or Firm* — Armis IP Law, LLC (57) ABSTRACT

A biomaterial collection system has a receptacle, pouch or bag for collection and a status detection device for indicating pouch volume based on a distance between opposed sides or panels of the receptacle. The receptacle is a collection vessel having a sealed volume defined by at least two opposed panels, and an interior volume defined by a distance between the opposed panels. A detection circuit including a Hall effect sensor and rare-earth magnet provides a signal indicative of the distance. The collection vessel may be employed in conjunction with procedures such as ileostomy, urostomy and colostomy for indication of a nearly full collection vessel that requires emptying.

14 Claims, 11 Drawing Sheets

(58) Field of Classification Search
CPC ............ A61F 5/445; A61F 5/455; A61F 5/44;
A61M 2205/14; A61M 2205/18; A61M
2205/3317; A61M 2205/3515; A61M
5/1684; G08B 21/02; G08B 21/182
See application file for complete search history.

(56) References Cited

U.S. PATENT DOCUMENTS

| | | | |
|---|---|---|---|
| 2016/0067113 A1* | 3/2016 | Vartiainen | A61F 13/42 604/361 |
| 2017/0140103 A1* | 5/2017 | Angelides | A61F 5/4404 |
| 2017/0254693 A1* | 9/2017 | Sano | G01F 23/0023 |
| 2018/0214635 A1* | 8/2018 | Raman | A61M 5/172 |
| 2019/0365990 A1* | 12/2019 | Phillips | A61M 5/14248 |

FOREIGN PATENT DOCUMENTS

| | | |
|---|---|---|
| WO | 2019169327 A1 | 9/2019 |
| WO | WO-2019169327 A1 * | 9/2019 |

* cited by examiner

FIG. 1

```
                                    ┌─200
                                    ┌─201
┌──────────────────────────────────────────────────────────────────────────┐
│ ENGAGING A FLUID RECEPTACLE WITH A CONDUIT IN FLUID COMMUNICATION WITH   │
│ A VOLUME CONTAINED IN THE FLUID RECEPTACLE, THE FLUID RECEPTACLE HAVING  │
│   A PLURALITY OF FLEXIBLE PANELS DEFINING AN ENCLOSED INTERIOR FOR       │
│                         CONTAINING THE VOLUME                            │
└──────────────────────────────────────────────────────────────────────────┘
                                    │
                                    ▼                       ┌─202
┌──────────────────────────────────────────────────────────────────────────┐
│ RECEIVING A DISTANCE SIGNAL FROM A DISTANCE SENSOR ADHERED TO A PANEL OF │
│  THE FLUID RECEPTACLE, THE DISTANCE SIGNAL INDICATIVE OF A DISTANCE TO   │
│ ANOTHER OF THE PLURALITY OF FLEXIBLE PANELS, THE DISTANCE RESULTING FROM │
│                     A QUANTITY OF THE CONTAINED VOLUME                   │
└──────────────────────────────────────────────────────────────────────────┘
                                    │
                                    ▼                       ┌─203
┌──────────────────────────────────────────────────────────────────────────┐
│ COMPUTING, BASED ON THE DISTANCE SIGNAL, A VOLUME OF THE FLUID CONTAINED │
│                            IN THE RECEPTACLE                             │
└──────────────────────────────────────────────────────────────────────────┘
```

MAGNET CONFIGURATIONS

| POSITION (mm) | | 15x1.7mm x1 N? | | 15x1.7mm x2 N? | | 15x1.7mm x3 N? | |
|---|---|---|---|---|---|---|---|
| X | Y | SENSOR mT | | SENSOR mT | | SENSOR mT | |
| 999 | 999 | 769 | 0.0 | 768 | 0 | 769 | 0 |
| 0 | 0 | - | 109.0 | - | 163 | - | 210 |
| 24.73 | 0 | 793 | 1.4 | 813 | 2.6 | 846 | 4.5 |
| 37.39 | 0 | 777 | 0.5 | 784 | 0.9 | 796 | 1.5 |
| 50.05 | 0 | 773 | 0.2 | 776 | 0.4 | 781 | 0.7 |
| 62.71 | 0 | 771 | 0.1 | 772 | 0.2 | 775 | 0.3 |
| 75.37 | 0 | 770 | 0.0 | 771 | 0.1 | 773 | 0.2 |
| 88.03 | 0 | 769 | 0.0 | 770 | 0 | 771 | 0.1 |
| 62.71 | 12.6 | 771 | 0.1 | 772 | 0.2 | 775 | 0.3 |
| 62.71 | -12.6 | 771 | 0.1 | 772 | 0.1 | 775 | 0.3 |
| 37.39 | 25.4 | 772 | 0.2 | 776 | 0.4 | 780 | 0.5 |
| 37.39 | -25.4 | 772 | 0.1 | 774 | 0.2 | 778 | 0.5 |
| 88.03 | 25.4 | 770 | 0.0 | 770 | 0 | 770 | 0.1 |
| 88.03 | -25.4 | 769 | 0.0 | 770 | 0 | 770 | 0.1 |

FIG. 11

OSTOMY COLLECTION STATUS DETECTOR

RELATED APPLICATIONS

This patent application claims the benefit under 35 U.S.C. § 119(e) of U.S. Provisional Patent App. No. 62/943,426, filed Dec. 4, 2019, entitled "OSTOMY COLLECTION STATUS DETECTOR," incorporated herein by reference in entirety.

BACKGROUND

Ostomy collection systems are post-surgical arrangements for collection of bodily wastes based on a surgically diverted biological stream. An ostomy pouching system is a prosthetic medical device that externally interfaces with a stoma, or surgically created exit, for retaining expelled material into a pouch or bag from which they may be disposed. Pouching systems are often associated with colostomies, ileostomies, and urostomies. A collection pouch interfaces with an engagement barrier that secured to a dermal surface of a patient by adhesive and/or belted means. Periodic collection prior to overflow prevents a breach of the collection system.

SUMMARY

A biomaterial collection system with overflow detection has a receptacle, pouch or bag for collection of biomaterial output from a stoma. and a status detection device for indicating excessive bag volume based on a distance between opposed sides or panels of the receptacle. The receptacle is a collection vessel defining a sealed containment defined by at least two opposed panels, and an interior volume defined by a distance between the opposed panels. The collection vessel may be employed in conjunction with or after procedures such as ileostomy, urostomy and colostomy for indication of a nearly full collection vessel that requires emptying. A sensor apparatus is disposed on at least one of the panels and is configured for identifying a fluidic occupancy of the interior volume based on detecting a distance between the opposed panels. The sensor apparatus includes a first component on a first panel of the opposed panel and a second component on a second panel of the opposed panels, such that the first component is configured for generating a value based on a distance to the second component. In one configuration, a detection circuit including a Hall effect sensor and rare-earth magnet provides a signal indicative of the distance. Due to the planar construction of the bag, this distance tends to be indicative of a quantity of gastric contents or other contained materials for collection or dispensing from the bag.

The collection vessel generally takes the form of a flexible container having generally coplanar flexible plastic sheets fused or joined around the perimeter to allow expansion between the panels for fluidic collection. An inlet or opening formed at a seam or orifice allows inflow of discharged patient fluids, resulting in expansion of the plastic bag as the panels separate to create a void for the incoming gastric contents. The collection vessel adheres or attaches to the patient using an engagement barrier to define a fluidic connection to a surgically defined exit point. The engagement barrier is typical an epidermal adhesion that attaches the collection vessel to the patient. Excessive pressure and/or volume in the collection vessel can cause failure of the collection system, often at the engagement barrier. As the collection vessel fills, a distance between the panels increases. In an example configuration, the sensor apparatus is a Hall effect sensor and the first component is in magnetic communication with the second component, thus providing a signal based on the distance between the panels, the distance being indicative of the volume.

In further detail, the disclosed ostomy collection and overflow detection system performs a method for detecting a volume in a flexible liquid containment by engaging a fluid receptacle with a medical or surgical conduit for receiving a volume into the fluid receptacle, in which the fluid receptacle has 2 or more flexible panels defining an enclosed interior for containing the volume. The detection system receives a distance signal from a distance sensor adhered to a panel of the fluid receptacle, such that the distance signal is indicative of a distance to another of the plurality of flexible panels, in which the distance results from a quantity of the contained volume. Capacity logic computes, based on the distance signal, a volume of the fluid contained in the receptacle approaching an overflow level.

In particular configurations, the receptacle may be any suitable fluidic containment with a need for volume monitoring. An ostomy receptacle or bag for collection of gastric contents may be monitored for a fluid volume approaching a full volume. In addition to ostomy based collection, any suitable medical collection apparatus, such as catheter collectors, surgical drains and blood collection, for example, may also be employed. Other configurations may attach to an IV bag for measurement of drained fluid to indicate a depleted volume with capacity logic for computing, based on the distance signal, a volume of the fluid contained in the receptacle approaching an empty level.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 8A-8C show the detection device, receiver and magnet components;

DETAILED DESCRIPTION

Depicted below is an example of various configurations of a collection receptacle volume measurement and alarm apparatus suitable for use with any fluid collection or supply measurement context. Configurations herein are based, in part, on the observation that collection systems are often employed in medical contexts for accommodating a temporary or permanent redirection of physiological fluid generation, often for collection of biological materials. Such systems are usually for buffering or containing a fluidic accumulation for facilitating mobility or sleep, and require periodic emptying, draining or replacement, often depending on the nature of the fluid contained therein. Unfortunately, conventional approaches to collection systems suffer from the shortcoming that an overfilled collection repository can present sanitary and comfort complications, as the contained fluids often present biohazard and/or infection concerns. Accordingly, configurations herein substantially overcome the shortcomings of conventional collection systems by providing a system, method and apparatus for determining a volume and fill status of a collection receptacle, bag or pouch and rendering an audio and/or visual and/or electronic (e.g. BLUETOOTH® wireless communication protocol or WiFi) alarm in response to an approaching overflow condition.

Figure 1:
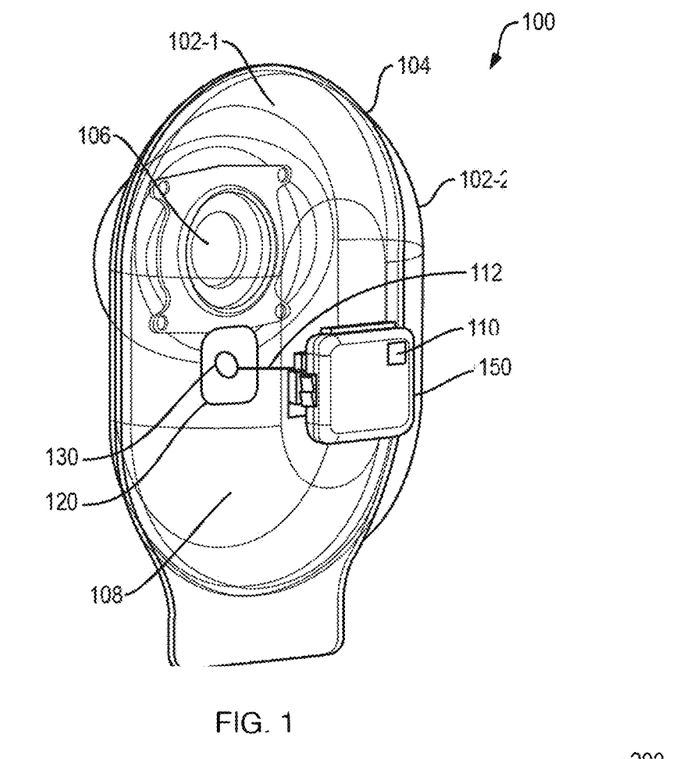
FIG. 1 is a perspective, transparent view of the volume detector device installed on an ostomy collection bag.

In a particular configuration, an ostomy collection system for gastric contents is beneficial for avoiding an overflow condition, particularly while sleeping or an ambulation situation where receptacle (bag) maintenance is sporadic. FIG. 1 is a perspective, transparent view of the volume detector device installed on a fluid receptacle 100 such as an ostomy collection bag 104. Fluidic volume detection as disclosed herein includes a fluid receptacle such as the collection receptacle 100 (bag) having a plurality of flexible panels 102-1 ... 102-2 (102 generally) defining an enclosed interior 108 for containing a volume of fluid. The detector device includes a detection module 110 including a distance sensor 150 attached to one of the flexible panels 102-1 and configured for detecting a distance to another of the plurality of flexible panels, such as panel 102-2. The detection module 110 includes volume logic for computing a volume of the fluid receptacle based on the detected distance, discussed further below.

The generally ovaloid shape of the collection receptacle 100 results from the two panels 102, each defined from a flexible material and oval shape such that upon filling, the ovaloid shape emerges as the fluid (typically liquid) fills the volume and disposes the panels 102 apart by a distance. The collection receptacle 100 generally includes at least two of the panels 102 arranged in an opposed manner, such that the distance sensor 150 is disposed on one of the opposed panels and configured for detecting the distance 112 to the opposed panel 102-2. Any suitable arrangement and shape of panels may be employed, with the preference that the detected distance results from panels 102 disposed apart from a quantity of the contained liquid.

The orifice 106 or opening allows inflow of the fluid for measurement. An example configuration deploys an ostomy collection bag, and the orifice is fluidically coupled to the ostomy for receiving gastric contents. The collection bag is adhered or strapped to the patient's ostomy by any suitable approach. In particular configurations, the attachment may include an adapter such as that disclosed in U.S. patent application Ser. No. 16/744,256, filed Jan. 16, 2020, entitled "Ostomy Skin Barrier Adapter."

The distance 112 is determined based on a marker 120 attached or adhered to the opposed panel 102-2. In the example arrangement, the distance sensor 150 is a magnetic flux sensor and the marker 120 on the opposed flexible panel 102-2 has a magnetic source 130, such that the detected distance is indicative of a distance from the magnetic flux sensor to the magnetic source 130. One particular configuration employs a Hall effect sensor disposed for receiving magnetic flux from the opposed flexible panel 102-2, and the magnetic source 130 includes a rare-earth magnet contained in the marker 120.

The Hall effect sensor provides a voltage. The Hall voltage is a measure of the magnetic flux density, which can vary based on two kinds of Hall-effect sensors: linear, which means that the output of voltage linearly depends on magnetic flux density; and threshold, which means that there is a sharp decrease of output voltage at some magnetic flux density. Other suitable distance sensing mediums may be employed. For example, an ultrasound sensor and sonic emitting source, or an infrared (IR) medium and photodetector are operable if the contained liquid is sufficiently clear. An electromagnetic medium of any suitable wavelength may also be employed as long as power and range aspects are appropriate.

Figure 2:
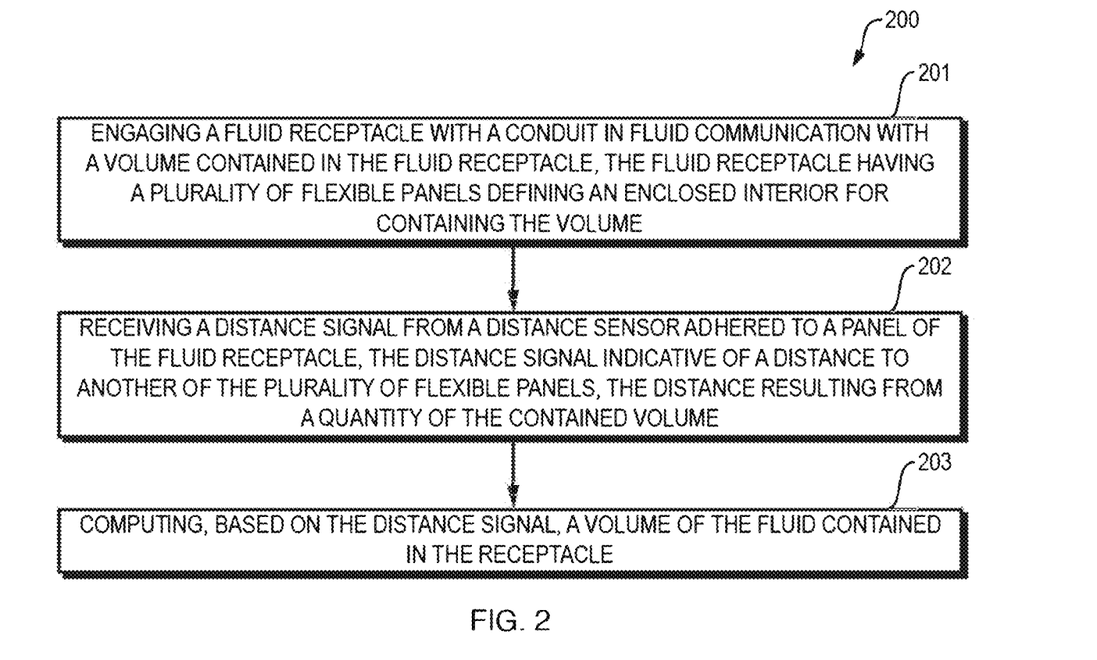
FIG. 2 is a flowchart of volume detection in the device of FIG. 1.

FIG. 2 is a flowchart 200 of volume detection in the apparatus and device of FIG. 1. At step 201, the method for detecting a volume in a flexible liquid containment includes engaging the collection receptacle 100 with a conduit in fluid communication for filling the collection receptacle, such as the orifice 106 positioned at a surgical stoma. A distance computation circuit receives a distance signal from a distance sensor 150 adhered to a panel 102 of the fluid receptacle 100, such that the distance signal is indicative of a distance to another of the plurality of flexible panels. The distance results from a quantity of the contained volume, as depicted at step 202. In the above example, the distance signal is a voltage level indicating the magnetic flux sensed or measured from the opposed magnetic source 130 (magnet), which decreases inversely with the distance 112. The distance computation circuit computes, based on the distance signal, a volume of the fluid contained in the receptacle, as disclosed at step 203.

Figure 3:
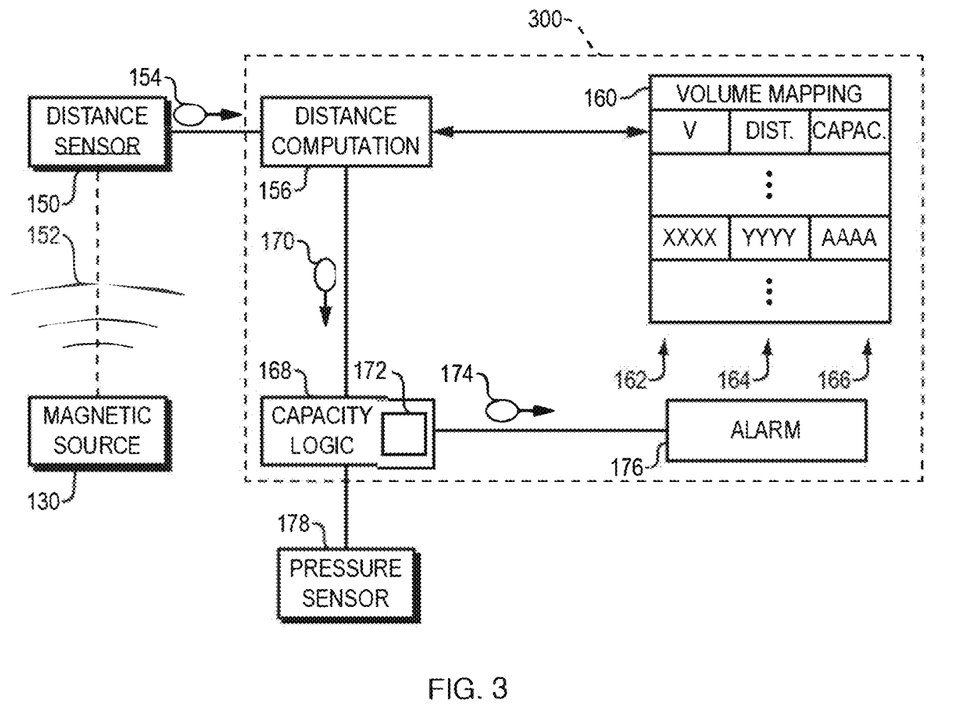
FIG. 3 is a block diagram of the detector device of FIGS. 1 and 2.

FIG. 3 is a block diagram of the detector device depicted in FIGS. 1 and 2. Referring to FIGS. 1-3, a detection circuit 300 is configured for mapping the detected distance 112 to a volume, such that the volume is based on a capacity of the fluid receptacle 100 when the panels 102 are separated by the detected distance. The detection circuit 300 includes a distance computation circuit 156 and capacity logic 168. The distance sensor 150 receives a magnetic flux 152 from the magnetic source 130, and sends a corresponding distance signal 154 to the distance computation circuit 156.

In the example arrangement, the detection circuit has a mapping table 160 of distance values 164 and corresponding volume values 166, such that the distance values define a sequence of incremental separation of the panels 102. The distance computation circuit 156 is configured for identifying the volume mapped from one of the distance values in the sequence based on the mapping table 160. The mapping table 160 relates voltage levels 162 to a distance field 164 calibrated for the distance 112. The dimensions of the fluid receptacle 100 determine the capacity 166 at a particular distance. In general, basic geometry indicates that, for similar sized parallel panels 102, the area multiplied by the distance gives an interior volume for containing fluid. While capacity may be computed somewhat accurately by this relation, the capacity 166 is stored for increments of distance to accommodate for curvature and flexures of the oval shape of the panels 102, and for effects of gravity on a free flowing liquid volume contained in a resilient or flexible pouch.

An alternate configuration may employ a pressure sensor 178, which detects a pressure of the repository 100 contents, which may occur if the bag is compressed (e.g. sat on, rolled on by a sleeping patient) prior to complete filling. The pressure sensor 178 is disposed in communication with the receptacle 100 or on a circumferential band for sensing a pressure of the fluid receptacle. The detection circuit 300 couples to the pressure sensor for rendering the alarm signal based on the pressure sensor.

Capacity logic 168 receives the current computed volume level 170 for comparison with an alarm threshold 172. The capacity logic further comprises an alarm threshold 172 based on a volume, and the detection circuit is operable to render an alarm signal when the volume exceeds the alarm threshold. The threshold 172 indicates a fluid volume level 170 approaching an overflow level, such as 80% of maximum volume or capacity. The threshold may also have multiple tiers, such as 75% full, 90% full, and other levels as needed. If the received level 170 exceeds the threshold 172, the capacity logic 168 sends an alarm signal 174 to an alarm 176, which renders an audible and/or visual and/or electronic signal signaling needed attention for emptying or changing the fluid receptacle 100. Other suitable annunciator actions may include, for example, a BLUETOOTH transmission, text message or email for directing remedial action. Other use cases may include a monitoring dashboard system in a healthcare facility (such as a nursing home or hospital) at a nurses station to monitor the ostomy displacement status. Oversight of multiple ostomy patients in the ward provides a centralized alarm station to monitor the cohort of ostomy collection systems with pending emptying needs. In a hospital environment, for example, the alarm system with similar configuration but modified detection threshold computations may be used to monitor the fullness status of fluid containing bags as they empty, such as IV bags. When combined with wireless communication technology, the alarm system could be deployed in the hospital wards to assist healthcare teams to remotely monitor the status of intravenous administration of medications to patients.

Figure 4A:
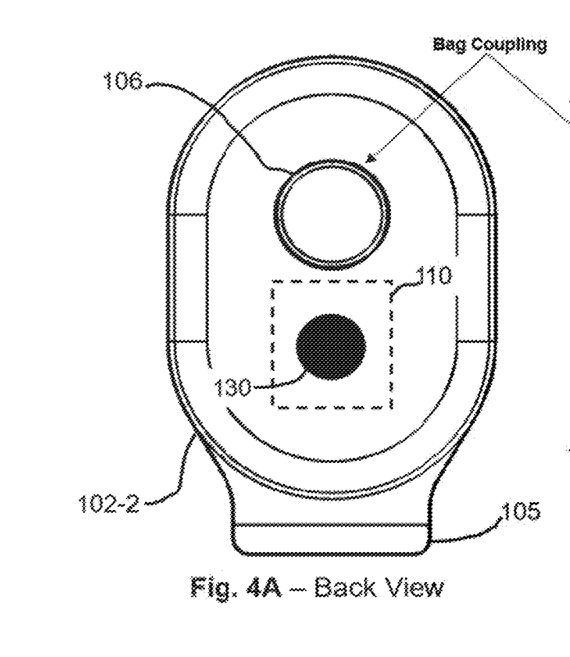
FIGS. 4A-4D are a schematic diagram of the detector device of FIG. 1.
Figure 4B:
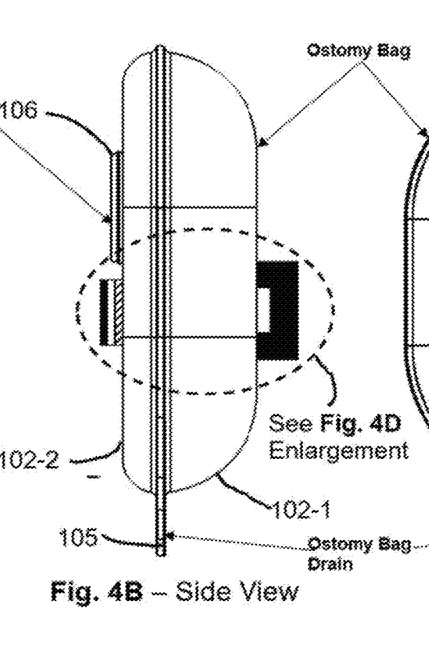
Figure 4C:
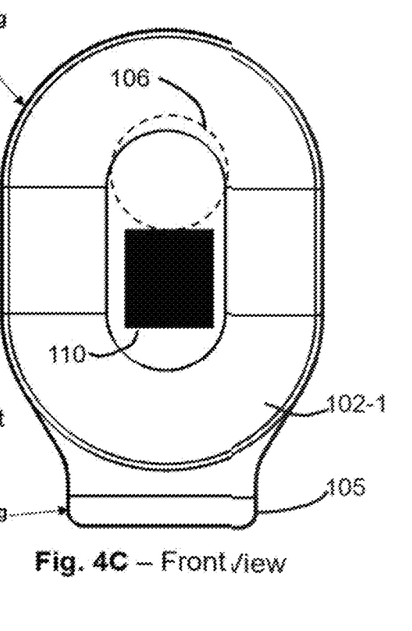
Figure 4D:
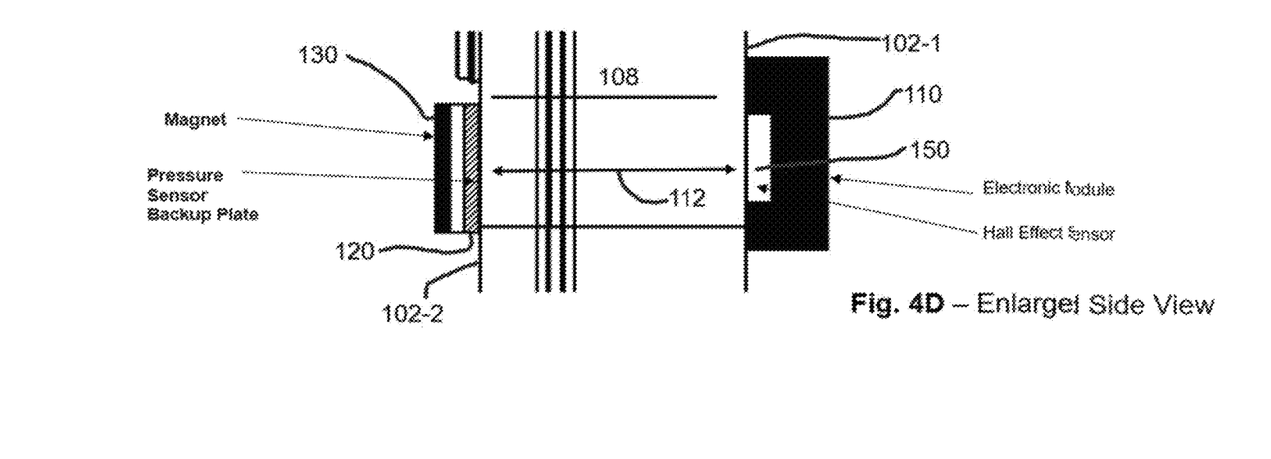

FIGS. 4A-4D are a schematic diagram of the detector device of FIG. 1. Referring to FIGS. 1-3 and 4A-4D, the panel 102-2 forms a back panel as shown in FIG. 4A, and panel 102-1 forms a front panel, which are joined, glued or fused to form the enclosed interior 108. The magnetic source 130 aligns with the distance sensor 150 in the detection module 110 when the collection receptacle 100 is empty, and remains generally aligned in an opposed manner, however slight angular deviations may occur as the bag fills, discussed further below. The magnet is disposed just below the orifice 106, and a drain 105 allows emptying as with most conventional collection bags. FIG. 4D shows the alignment of the magnetic source 130 (magnet) and distance sensor 150 separated by a distance 112 across the interior 108. It follows that as the interior expands to accommodate inflow, the distance 112 increases generally proportionally and based on the dimensions of the fused panels 102.

Figure 5:
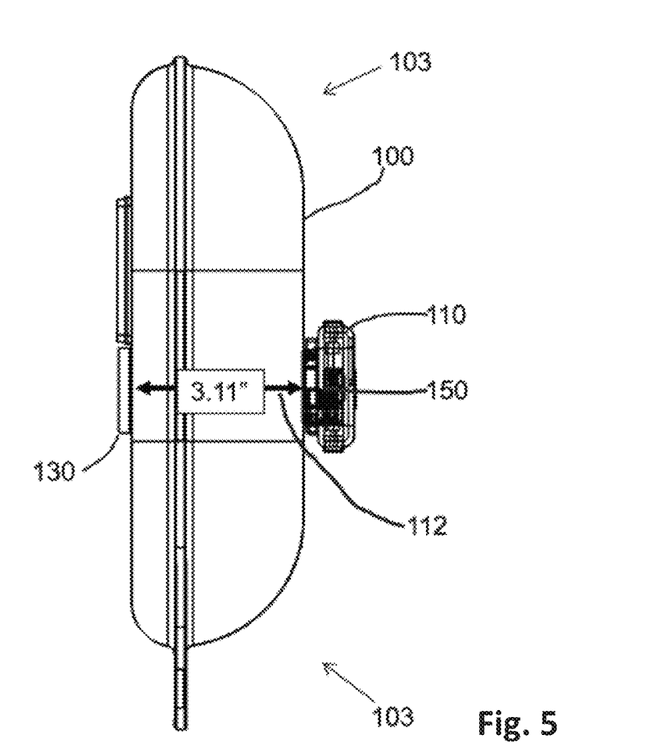
FIG. 5 shows deployed limits of the detection device of FIGS. 1-4D.

FIG. 5 shows deployed limits of the detection device of FIGS. 1-4D. Referring to FIGS. 4A-5, a maximally expanded (filled) collection receptacle is shown to have a distance of 3.11" for a particular representative configuration. The detection module 110 and marker 120 may integrate with various common sizes and shapes of collection bags, which may vary somewhat in dimension, maximum capacity and filled distance 112. The mapping table 160 may be calibrated for particular distance values 164 associated with a bag of a specific vendor, however a small deviation from size parameters will not impede operation, e.g. one vendor's 75% capacity may be another vendor's 80% capacity. FIG. 5 also illustrates a curvature 103 that results from panel 102 shape and flexibility, which causes the interior 108 to deviate from a mathematical volume computation based on an ideal cube shape. While mathematical computations based on area and distance 112 would likely provide a close approximation, the mapping table 160 allows greater precision and granularity of filling increments.

In particular configurations, an array of Hall effect sensors, either individual units or a self-contained Hall array module can be used to detect the orientation of the magnet in cases where the magnet becomes oriented off-axis with the sensor unit. By using a Hall array, magnetic field strength and orientation are known, and combined with a known magnet strength, can be used to calculate the position of the magnet at differing orientations for mitigating deviation from a shortest-path distance that assumes purely parallel orientation of the opposed panels 102.

Figure 6:
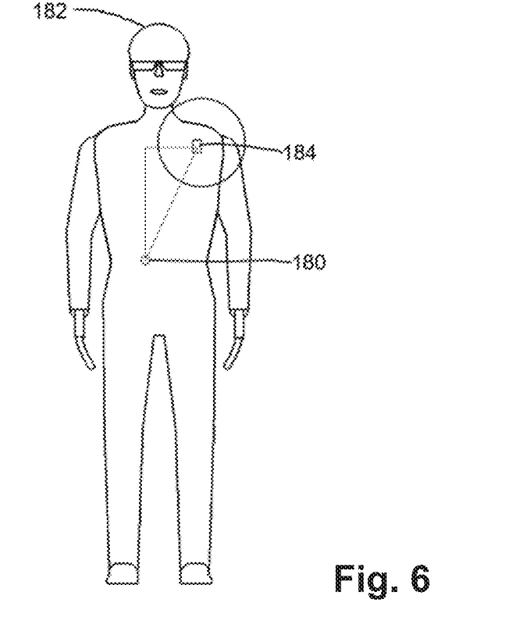
FIG. 6 shows a patient deployment in the ostomy configuration of FIGS. 1-5.

FIG. 6 shows a patient deployment in the ostomy configuration of FIGS. 1-5. Referring to FIGS. 4A and 6, the location of the orifice 106 disposes the magnet just below the surgical stoma 180 of the patient 182. The magnetic source 130 has a magnetic flux 152 magnitude based on a distance from a location of a stoma 180 defining an installed location of the fluid receptacle 100. Magnetic strength imposed by the magnetic source 130 should be considered with respect to any other installed medical devices. For example, pacemakers are a common occurrence; the placement of the device should be distal from a location of a surgically installed cardiac appliance, in which the cardiac appliance may be sensitive to the magnetic flux 152. As the stoma is generally disposed based on the lower gastrointestinal tract of the patient 182, this placement ensures that the marker magnetic source 130 is sufficiently distal from placement of a typical pacemaker 184 for ensuring no adverse magnetic interference.

Figure 7:
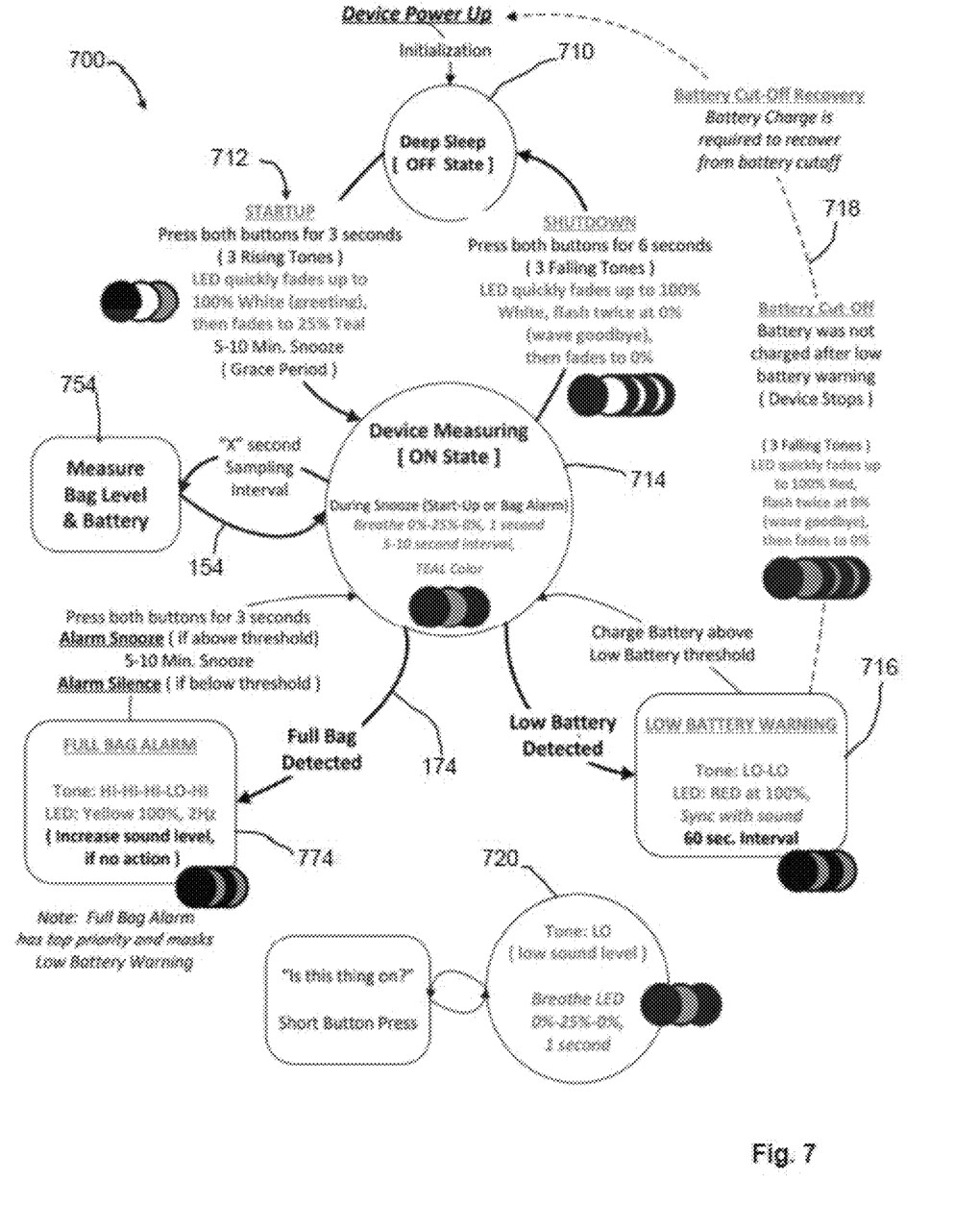
FIG. 7 shows operation and detection logic of the device of FIGS. 1-6.

FIG. 7 shows operation and detection logic of the device of FIGS. 1-6. Referring to FIGS. 3 and 7, the detection module 110 has control electronics including the distance computation circuit 156, the capacity logic 168 and other controls and user interfaces. Referring to FIGS. 1, 3 and 7, an operational state diagram 700 includes a device power up, transitioning from an off/sleep state 710 to a startup state 712. This commences a device measuring state 714, during which measurement operations 754 occur iteratively with the distance signal 154 processed at periodic intervals. A power saving feature may employ adaptive sampling such that the frequency of polling the Hall effect sensor is varied as a function of bag displacement, rate of change of bag displacement and/or acceleration of bag displacement. If the capacity logic 168 concludes a threshold 172 is attained, then a full bag alarm state 774 is triggered by the alarm signal 174.

A low battery state 716 occurs if a power supply (typically a rechargeable lithium cell) degrades, commencing a battery cut-off and restart sequence 718. A separate activation check state 720 can be initiated at any time to confirm that the measuring state 714 is engaged and monitoring bag contents.

A data recording feature may log or transmit a fill profile of the bag over time. A profile of data points may be recorded and can be made available to the user to gain a better understanding of their digestive output profile, and to monitor changes to the output profile.

A user interface or GUI (Graphical User Interface) may be provided, for example as an app on a mobile device or laptop, and coupled via a USB port. This GUI would allow the user to modify the detection/alarm system threshold to alarm at a variable displacement. The user may also increase the frequency of measurements taken such as in the case of large, sudden output into the ostomy collection system.

Figure 8A:
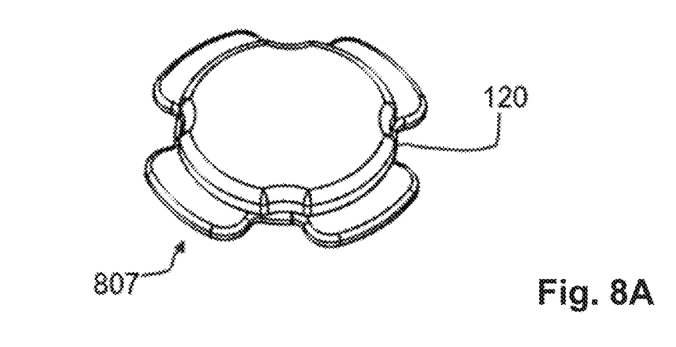
Figure 8B:
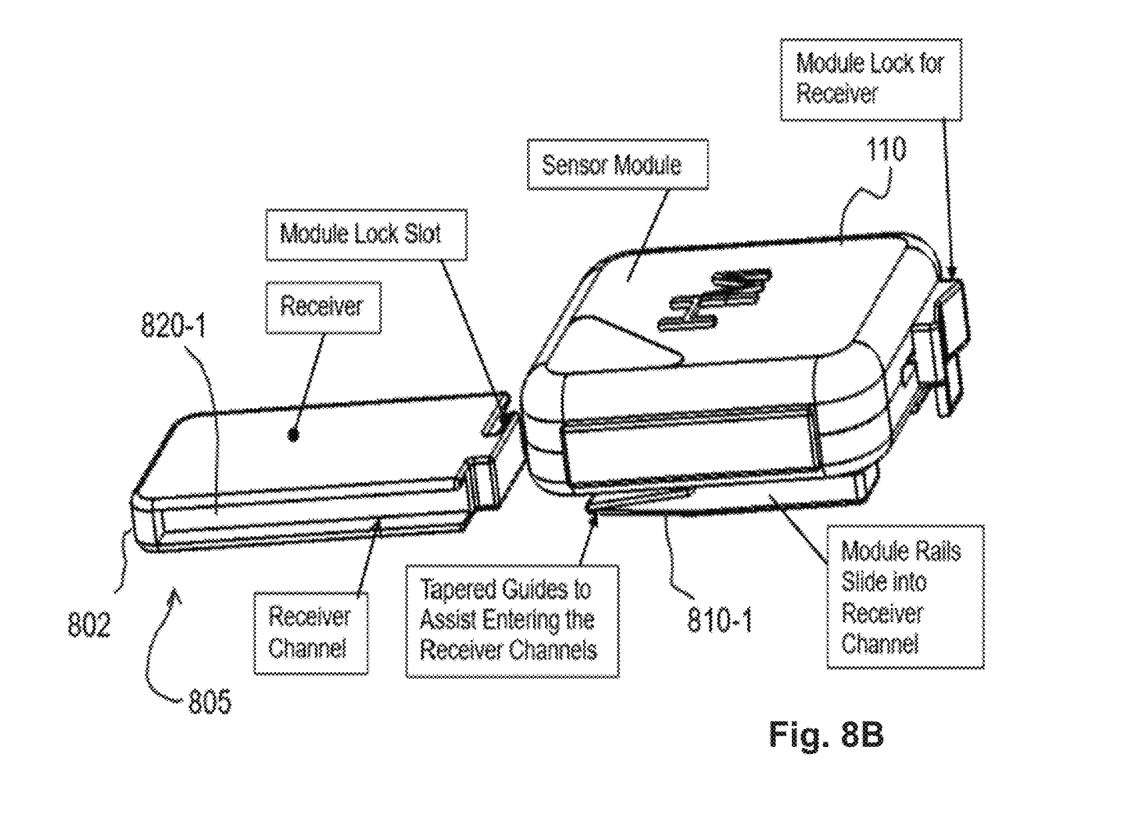

FIGS. 8A-8C show the detection device, receiver and magnetic components. The detection module 110 encapsulates the distance sensor 150 and detection circuit 300 in a deployable package in conjunction with the collection receptacle 100, and may take several forms which will now be discussed. Ostomy bags are consumable healthcare appliances, and the detection module 110 and marker 120 may be adhered, molded, attached and/or integrated with a suitable collection receptacle 100 by a variety of mechanical and manufacturing approaches. In the particular examples herein, referring to FIGS. 1-3 and 8A-8C, the detection module 110 is adapted to engage a receiver 802 attached to one of the flexible panels 102 and adapted for slidable engagement with the detection module 110. Selective engagement of the detection module allows product longevity when paired with a single or limited use collection receptacle; the receiver 802 is likewise a low-cost disposable element. The collection receptacle 100 may attach via an adhesive region 805 on the receiver 802, such that the adhesive region 805 secures the receiver to the flexible panel 102. The marker 120 has a similar adhesive region 807 for affixing the magnetic source 130 in alignment. Alternatively, the receiver 802 may be molded into the collection receptacle 100 as part of a manufacturing process, and the marker may be similarly attached.

To facilitate separation and reuse, the detection module 110 has a pair of elongated, parallel rails 810-1 . . . 810-2 (810 generally) and the receiver 802 has a pair of parallel channels 820-1 . . . 820-2 (820 generally). The parallel channels 820 define slots for slidably engaging the rails 810 and secure the module 110 with a lip 812 that underrides an upper edge of the channels 820.

Figure 9A:
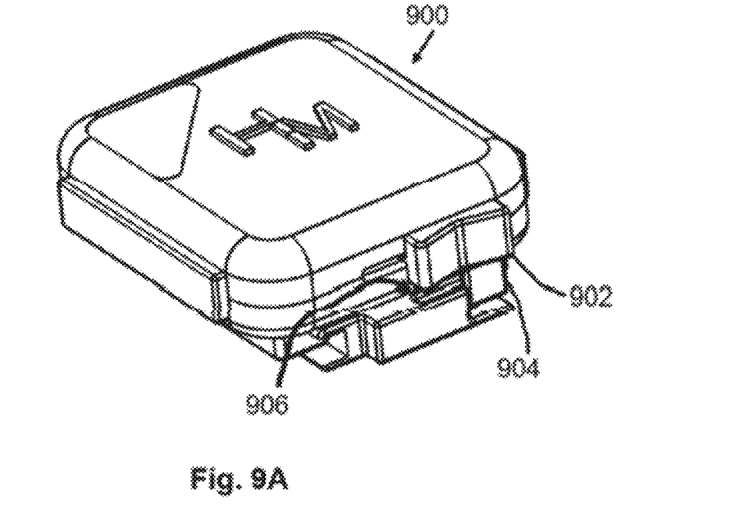
FIGS. 9A-9B show a locking engagement with the receiver of FIGS. 8B-8C.
Figure 9B:
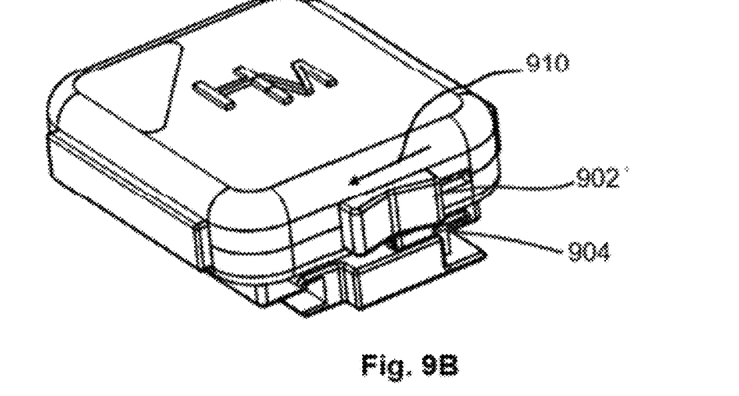

FIGS. 9A-9B show a locking engagement with the receiver of FIGS. 8B-8C. Referring to FIGS. 1 and 8A-9B, the engaged receiver 802 and detection module 110 form a secured unit 900 affixed to the panel 102, complemented by the magnet 130 on the opposite panel. The module 110 further includes a locking tab 902 for securing the detection module 110 from inadvertently sliding out of the receiver 802. The locking tab 902 is adapted to be disposed into an interference fit in a slot 906 for preventing retraction of the parallel rails 810 from the parallel channels 820. Once fully inserted, the locking tab 902 is disposed in the direction of arrow 910 to position 902' such that a protrusion 904 engages the slot 906 for preventing retraction of the module 110 unless the locking tab 902' is disengaged.

Figure 10A:
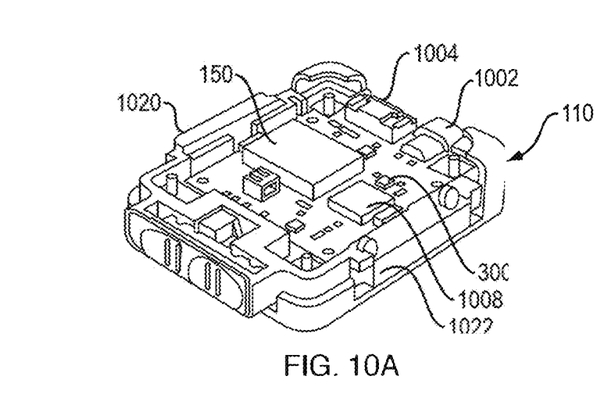
FIGS. 10A-10C show internal circuits in the device of FIGS. 1-9B.
Figure 10B:
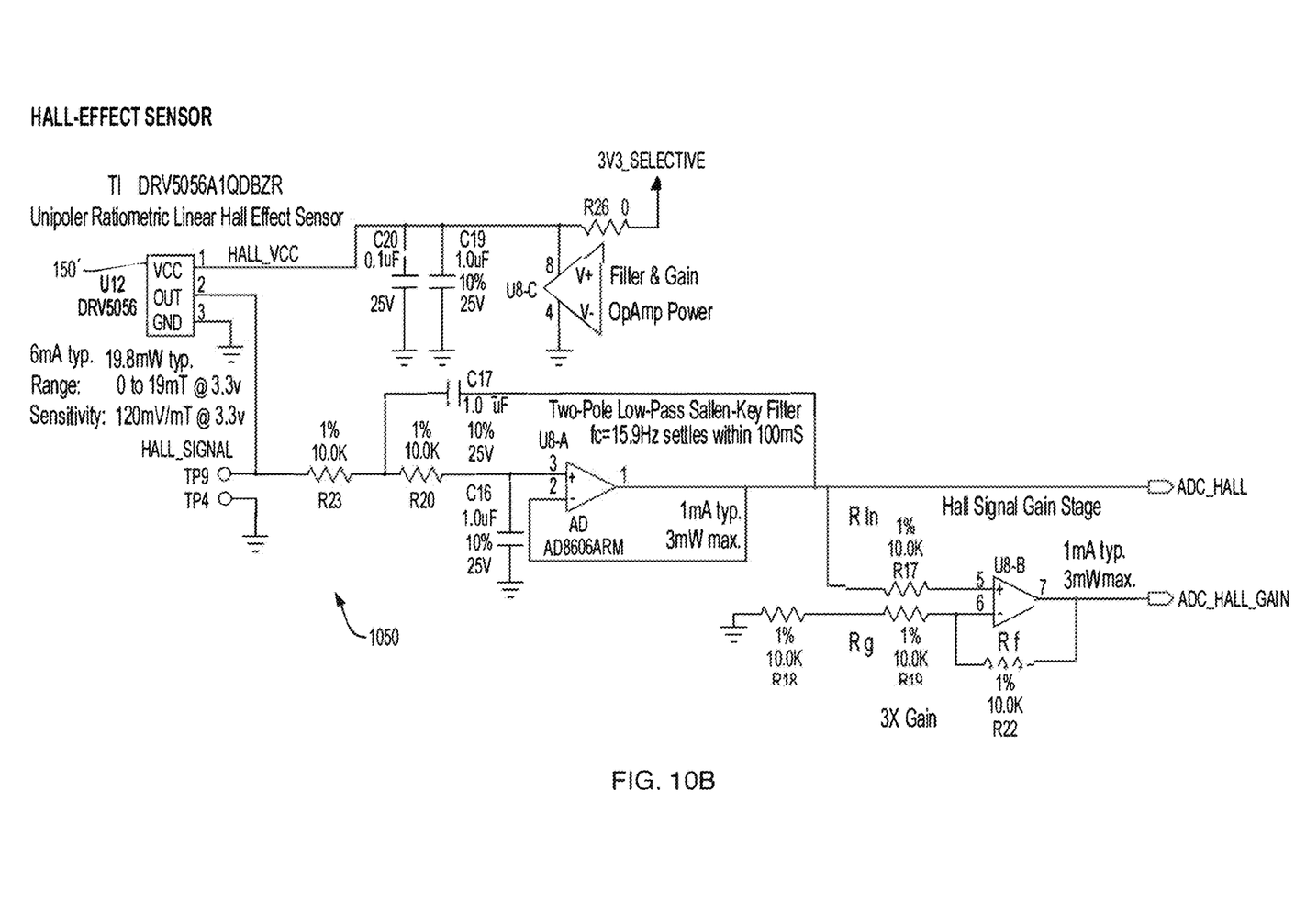
Figure 10C:
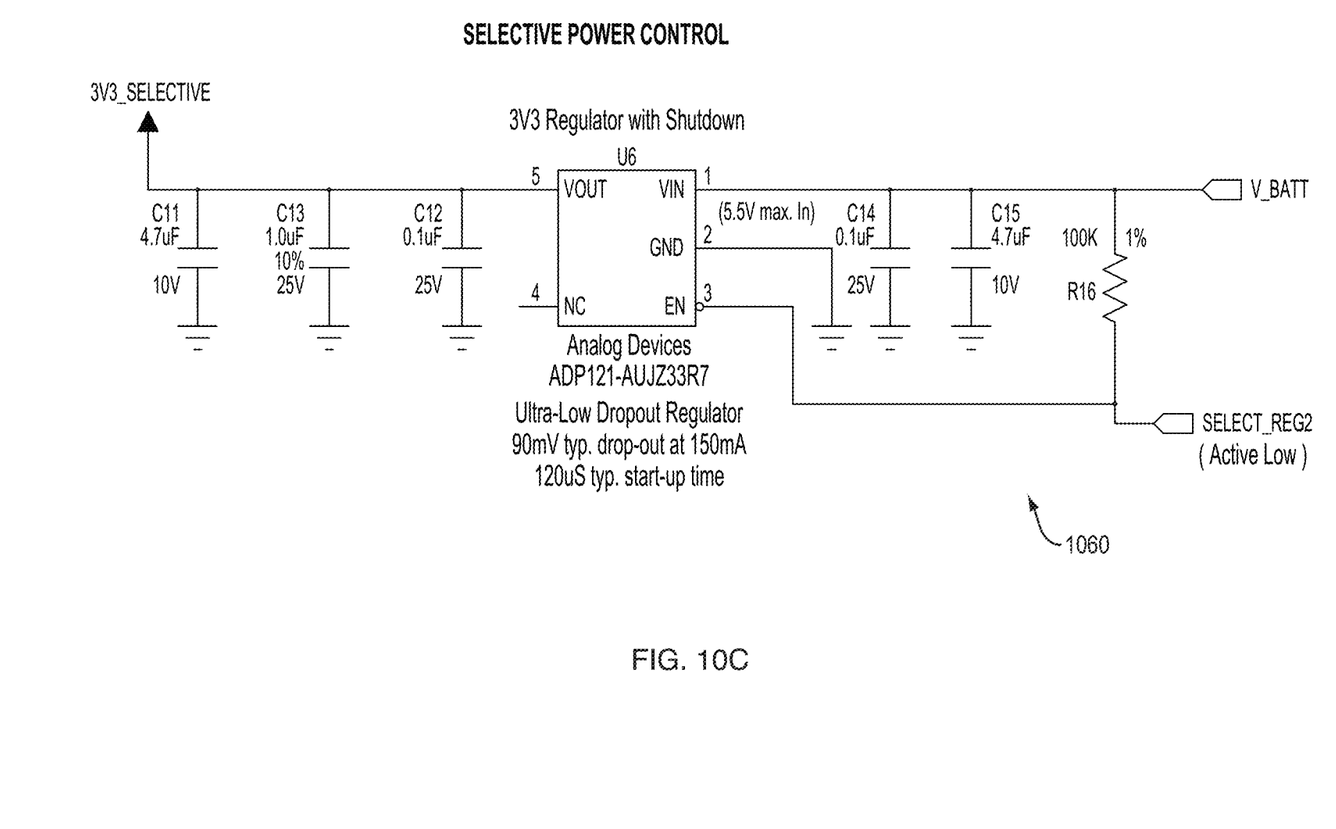

FIGS. 10A-10C show internal circuits in the device of FIGS. 1-9B. Referring to FIGS. 3, 7 and 10A-C, the detection module 110 packages the detection circuit 300, distance sensor 150 and related components. The detection module 110 further encapsulates a memory 1008 for storing the volume logic, the detection circuit 300, which is coupled to the distance sensor 150 for receiving the distance signal 154 and a power supply for powering the memory 1008 and the detection circuit 300. Other components include a USB connector 1002 for optional I/O or remote activities, an optional multi-pin test port 1004, switches 1020, 1022 for operational input as disclosed in FIG. 7 and LEDs or visual indicators. The illustration is exemplary; a variety of suitable hardware and software components may be employed for implementing the disclosed device and operation.

In the particular configuration, FIG. 10B shows a portion of the sensor 150 circuit 1050, and FIG. 10C shows a portion of the power control circuit 1060. As discussed above, the disclosed configuration employs a Hall effect sensor 150' as the distance sensor 150.

Figure 11:
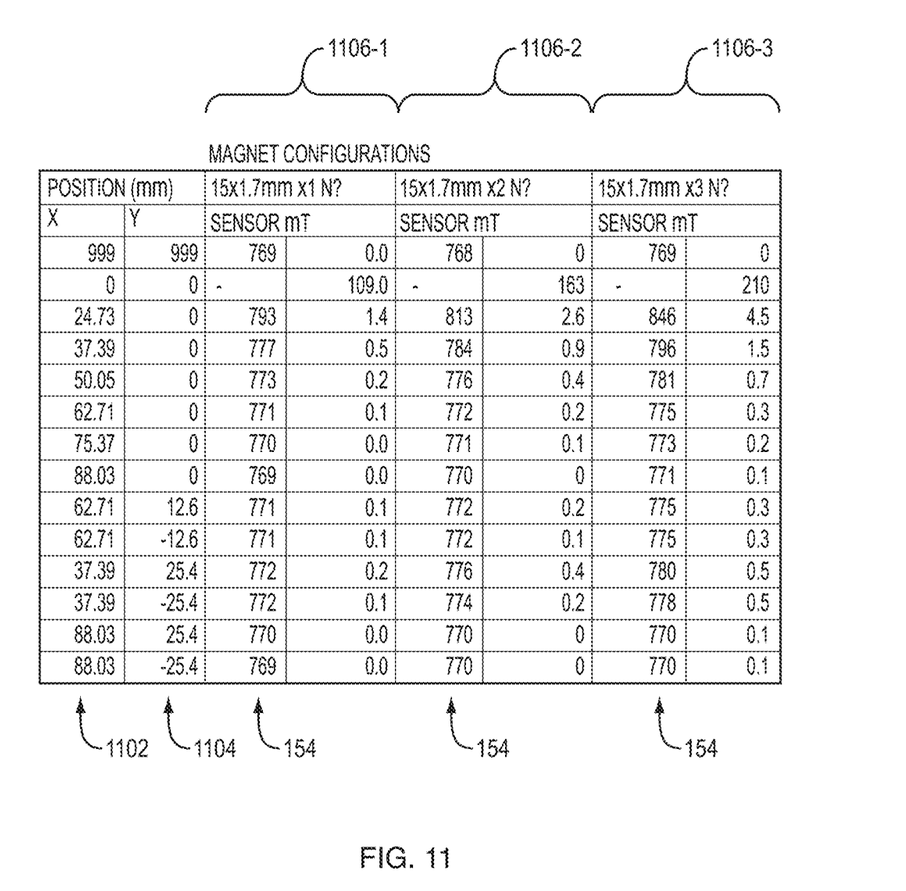
FIG. 11 shows example sensor outputs and corresponding magnetic field strength in operation of the device of FIGS. 1-10C.

FIG. 11 shows example sensor outputs and corresponding magnetic field strength in operation of the device of FIGS. 1-10C. Referring to FIGS. 3 and 11, the data and readings in the table show differing rare-earth magnet configurations for the magnetic source 130, and at different positions from the Hall effect sensor 150', shown by position coordinates 1102, 1104. The magnet configurations include a number of 15*1.7 mm neodymium magnets stacked in configurations of 1, 2, and 3 for columns 1106-1, 1106-2 and 1106-3, respectively. The disclosed magnet size is exemplary; a variety of suitable magnet configurations may be employed to achieve the desired magnetic field strength and dimensions.

For each magnet configuration 1106, the distance signal 154 at respective coordinates is shown along with a magnetic field strength mT as recorded with a Gaussmeter. Depending on the distance signal 154 for a specific receptacle configuration, the filled volume can be computed for population of the capacity 166.

Those skilled in the art should readily appreciate that the programs and methods defined herein are deliverable to a user processing and rendering device in many forms, including but not limited to a) information permanently stored on non-writeable storage media such as ROM devices, b) information alterably stored on writeable non-transitory storage media such as solid state drives (SSDs) and media, flash drives, floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions, including virtual machines and hypervisor controlled execution environments. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A volume detection device, comprising:
  a fluid receptacle having a plurality of flexible panels defining an enclosed interior for containing a volume; and a detection module, including:
    a distance sensor attached to at least one of the flexible panels and configured for detecting a distance to another of the plurality of flexible panels based on a magnetic sensing medium;
    a detection circuit coupled to the distance sensor for receiving a distance signal and configured for mapping the detected distance to a volume;

volume logic for determining a volume of the fluid contained in the receptacle based on the detected distance;

a memory for storing the volume logic; and a power supply for powering the memory and the detection circuit;

the detection circuit including a mapping table of distance values and corresponding volume values, the distance values defined by a sequence of incremental separation of the flexible panels including an off-axis sensed voltage that deviates from a shortest path distance, the detection circuit configured for identifying the volume mapped from one of the distance values in the sequence, the volume based on a capacity of the fluid receptacle when the flexible panels are separated by the detected distance.

2. The device of claim 1 wherein at least two of the flexible panels are arranged in an opposed manner, the distance sensor disposed on one of the opposed flexible panels and configured for detecting the distance to the opposed flexible panel.

3. The device of claim 1 wherein the distance sensor includes a magnetic flux sensor and another of the flexible panels has a magnetic source, a detected magnetic flux density being indicative of a distance from the magnetic flux sensor to the magnetic source.

4. The device of claim 3 wherein the magnetic source is located sufficiently distal from an installed medical appliance for ensuring no adverse magnetic interference, the installed medical appliance sensitive to the magnetic flux.

5. The device of claim 1 wherein the magnetic sensing medium includes one or more Hall effect sensor(s) disposed for measuring magnetic flux density from an opposed flexible panel having a rare-earth magnet.

6. The device of claim 1 further comprising:
a receiver, the receiver attached to one of the flexible panels and adapted for slidable engagement with the detection module.

7. The device of claim 6 further comprising:
an adhesive region on the receiver, the adhesive region securing the receiver to the flexible panel.

8. The device of claim 6 wherein the receiver is molded into one of the flexible panels for engagement with the detection module.

9. The device of claim 6 wherein the detection module has a pair of elongated, parallel rails and the receiver has a pair of parallel channels, the parallel channels defining slots for slidably engaging the rails.

10. The device of claim 9 further comprising a locking tab, the locking tab adapted to be disposed into an interference fit preventing retraction of the parallel rails from the parallel channels.

11. The device of claim 1 wherein the detection circuit further comprises an alarm threshold, the alarm threshold based on a volume, the detection circuit operable to render an alarm signal when the volume exceeds the alarm threshold.

12. The device of claim 11 further comprising a pressure sensor, the pressure sensor disposed for sensing a pressure of the fluid receptacle, the detection circuit coupled to the pressure sensor for rendering the alarm signal based on the pressure sensor.

13. The device of claim 1 wherein the magnetic medium includes a magnetic source and a magnetic flux detector on respective opposed flexible panels.

14. The device of claim 1 wherein the mapping table includes distance values based on a position of the magnet at differing orientations for mitigating deviation from a shortest-path distance resulting from parallel orientation of the opposed panels.

* * * * *